United States Patent
Zhu

(10) Patent No.: US 7,158,831 B2
(45) Date of Patent: Jan. 2, 2007

(54) METHOD AND APPARATUS FOR CARDIAC PACING WITH VARIABLE SAFETY MARGIN

(75) Inventor: Qingsheng Zhu, Little Canada, MN (US)

(73) Assignee: Cardiac Pacemakers, Inc., St. Paul, MN (US)

(*) Notice: Subject to any disclaimer, the term of this patent is extended or adjusted under 35 U.S.C. 154(b) by 635 days.

(21) Appl. No.: 10/243,622

(22) Filed: Sep. 13, 2002

(65) Prior Publication Data

US 2004/0054382 A1    Mar. 18, 2004

(51) Int. Cl.
*A61N 1/362*    (2006.01)

(52) U.S. Cl. ............................ 607/28; 607/9; 607/11

(58) Field of Classification Search ............... 607/28
See application file for complete search history.

(56) References Cited

U.S. PATENT DOCUMENTS

| | | | | |
|---|---|---|---|---|
| 3,949,758 A * | 4/1976 | Jirak | ............ | 607/28 |
| 5,855,594 A | 1/1999 | Olive et al. | ............ | 607/28 |
| 6,016,446 A | 1/2000 | Belalcazar | ............ | 607/13 |
| 6,038,474 A | 3/2000 | Zhu et al. | ............ | 607/9 |
| 6,044,296 A | 3/2000 | Zhu et al. | ............ | 607/13 |
| 6,061,594 A | 5/2000 | Zhu et al. | ............ | 607/28 |
| 6,169,921 B1 | 1/2001 | KenKnight et al. | ............ | 607/4 |
| 6,192,275 B1 | 2/2001 | Zhu et al. | ............ | 607/28 |
| 6,275,731 B1 | 8/2001 | Zhu et al. | ............ | 607/9 |
| 6,298,269 B1 | 10/2001 | Sweeney | ............ | 607/28 |
| 6,363,281 B1 | 3/2002 | Zhu et al. | ............ | 607/28 |
| 6,456,882 B1 * | 9/2002 | Schloss | ............ | 607/28 |
| 6,473,649 B1 | 10/2002 | Gryzwa et al. | ............ | 607/28 |
| 6,512,953 B1 * | 1/2003 | Florio et al. | ............ | 607/28 |
| 6,539,262 B1 | 3/2003 | Sweeney | ............ | 607/28 |
| 6,618,621 B1 * | 9/2003 | Holmstrom | ............ | 607/28 |
| 6,714,820 B1 * | 3/2004 | Casset et al. | ............ | 607/28 |
| 2002/0078968 A1 | 6/2002 | Spinelli et al. | ............ | 128/906 |

FOREIGN PATENT DOCUMENTS

EP    1136098 A2    9/2001

* cited by examiner

*Primary Examiner*—George Manuel
*Assistant Examiner*—Nicole Kramer
(74) *Attorney, Agent, or Firm*—Schwegman, Lundberg, Woessner, & Kluth, P.A.

(57) ABSTRACT

A cardiac pacemaker in which a variable safety margin with respect to a capture threshold is employed in delivering pacing pulses. The safety margin of a pacing pulse is made to vary in accordance with the pattern of preceding intrinsic and paced beats. The pacing pulse energy is thereby maintained at a more optimum value with respect to the capture threshold.

20 Claims, 2 Drawing Sheets

METHOD AND APPARATUS FOR CARDIAC PACING WITH VARIABLE SAFETY MARGIN

FIELD OF THE INVENTION

This invention pertains to cardiac pacemakers and methods for their operation. In particular, the invention relates to the setting and adjustment of pacing parameters.

BACKGROUND

Implantable cardiac pacemakers are a class of cardiac rhythm management devices that provide electrical stimulation in the form of pacing pulses to selected chambers of the heart. (As the term is used herein, a pacemaker is any cardiac rhythm management device with a pacing functionality regardless of any additional functions it may perform such as cardioversion/defibrillation.) Most pacemakers are used in the treatment of bradycardia by enforcing a minimum heart rate. If functioning properly, the pacemaker makes up for a heart's inability to pace itself at an appropriate rhythm. Also included within the concept of cardiac rhythm is the manner and degree to which the heart chambers contract during a cardiac cycle to result in the efficient pumping of blood. Pacemakers have been developed which provide electrical pacing stimulation to one or both of the atria and/or ventricles at single or multiple sites during a cardiac cycle in an attempt to improve the coordination of atrial and/or ventricular contractions, termed cardiac resynchronization therapy. Such multiple paces are usually delivered to a heart chamber during a cardiac cycle with a pacing mode similar to that used for bradycardia pacing.

In order for a pacemaker to be effective, the paces delivered by the device must achieve "capture," which refers to causing sufficient depolarization of the myocardium that a propagating wave of excitation and contraction result (i.e., a heart beat). A pacing pulse that does not capture the heart is thus an ineffective pulse. This not only wastes energy from the limited energy resources (battery) of pacemaker, but can have deleterious physiological effects as well, since a demand pacemaker that is not achieving capture is not performing its function in enforcing a minimum heart rate and/or providing resynchronization therapy. A number of factors can determine whether a given pacing pulse will achieve capture, but the principal factor of concern here is the energy of the pulse, which is a function of the pulse's amplitude and duration. The minimum pacing pulse energy necessary to achieve capture by a particular pacing channel is referred to as the capture threshold. Programmable pacemakers enable the amplitude and pulse width of pacing pulses to be adjusted, along with other parameters. It is common practice to determine the capture threshold by initially pacing with a high energy to ensure capture and then progressively lowering the pacing pulse energy during a sequence of cardiac cycles until capture is no longer achieved. The pacing pulse energy can then be adjusted to an appropriate value in accordance with the determined capture threshold by setting it equal to the capture threshold plus a specified safety margin. Ideally, the safety margin should be large enough to reliably pace the heart but small enough to minimize energy drain and thus prolong battery life.

SUMMARY OF THE INVENTION

The present invention is a cardiac pacemaker and operating method in which a variable safety margin is employed in delivering pacing pulses. It can be shown that capture by a pacing pulse is facilitated by prior pacing with capture as opposed to intrinsic activity. The pacing pulse energy can therefore be optimized if it is made to vary in accordance with the pattern of preceding intrinsic and paced beats. In an exemplary embodiment, a pacemaker is configured to deliver one or more pacing pulses to a heart chamber during a cardiac cycle in accordance with an inhibited demand pacing mode. The device is then further programmed to deliver a pacing pulse to the heart chamber with a pulse energy selected to exceed a specified capture threshold value by a first safety margin SM1 if the preceding N cardiac cycles were all paced cycles or by a second safety margin SM2 otherwise, where N is a specified integer and SM1 is less than SM2. Each of the individual safety margins SM1 and SM2 may also be dynamically adjusted in accordance with the results of capture verification tests performed while pacing.

DETAILED DESCRIPTION

Figure 1:
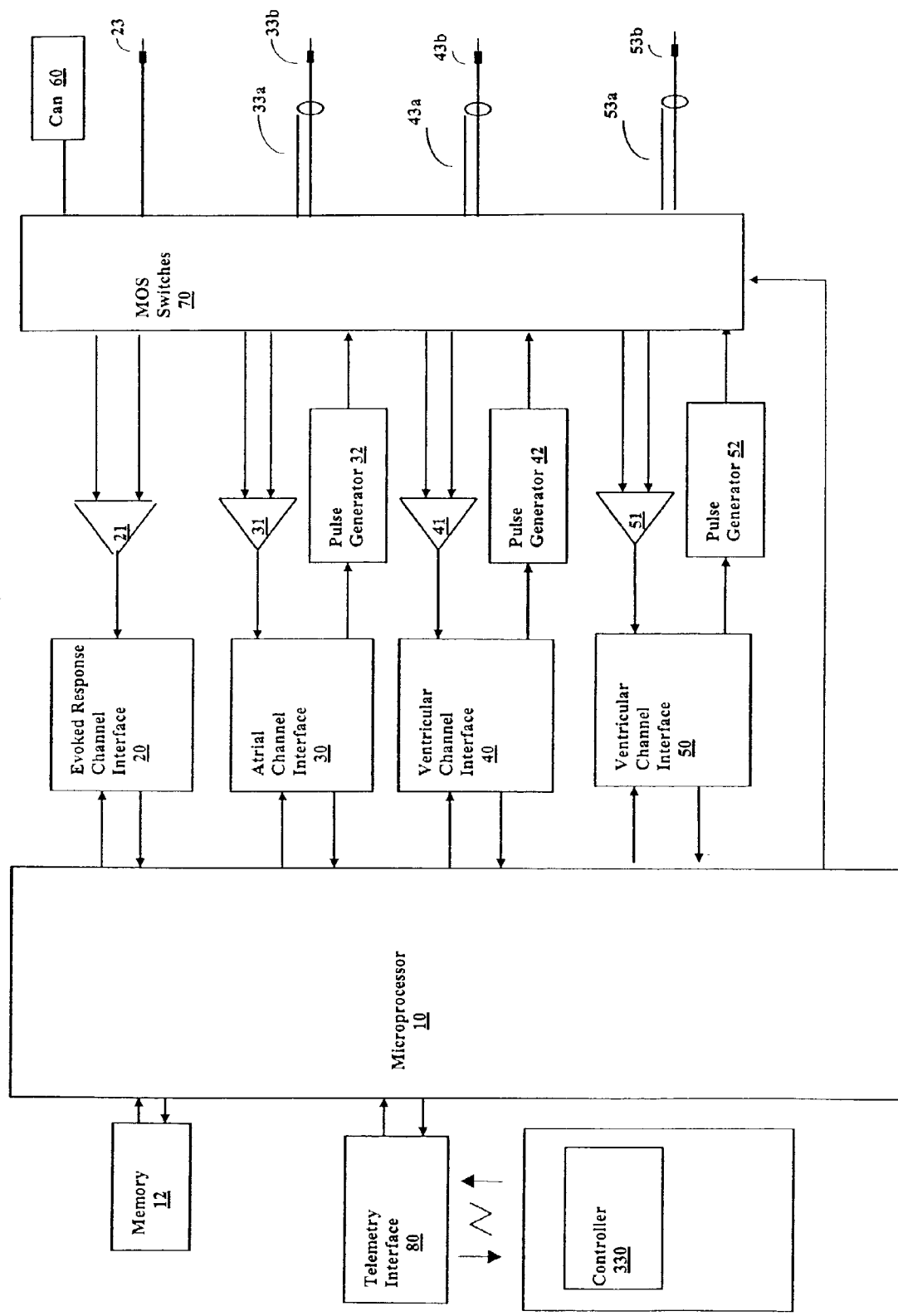
FIG. 1 is a block diagram of a multi-site pacemaker.

The present invention may be incorporated into pacemakers having a number of different pacing configurations, including multi-site pacing configurations for delivering various types of resynchronization therapy where a pace is delivered to each of the paired atria and/or ventricles during a cardiac cycle or where multiple paces are delivered to a single chamber. For illustrative purposes, however, a the invention will be described with reference to a dual-chamber pacemaker (i.e., one that senses and/or paces both the atria and ventricles) having two ventricular pacing channels for pacing both ventricles or delivering two paces to a single ventricle as shown in FIG. 1.

a. Hardware Platform

Pacemakers are typically implanted subcutaneously on a patient's chest and have leads threaded intravenously into the heart to connect the device to electrodes used for sensing and pacing. A programmable electronic controller causes the pacing pulses to be output in response to lapsed time intervals and sensed electrical activity (i.e., intrinsic heart beats not as a result of a pacing pulse). Pacemakers sense intrinsic cardiac electrical activity by means of internal electrodes disposed near the chamber to be sensed. A depolarization wave associated with an intrinsic contraction of the atria or ventricles that is detected by the pacemaker is referred to as an atrial sense or ventricular sense, respectively. In order to cause such a contraction in the absence of an intrinsic beat, a pacing pulse (either an atrial pace or a ventricular pace) with energy above the capture threshold must be delivered to the chamber.

The controller of the pacemaker is made up of a microprocessor 10 communicating with a memory 12, where the memory 12 may comprise a ROM (read-only memory) for program storage and a RAM (random-access memory) for data storage. The controller could be implemented by other types of logic circuitry (e.g., discrete components or programmable logic arrays) using a state machine type of design, but a microprocessor-based system is preferable. As used herein, the term "circuitry" should be taken to refer to either discrete logic circuitry or to the programming of a microprocessor. A telemetry interface 80 is provided for communicating with an external programmer 300. The external programmer is a computerized device with a controller 330 that can interrogate the pacemaker and receive stored data as well as adjust the operating parameters of the pacemaker.

The controller is capable of operating the pacemaker in a number of programmed modes where a programmed mode defines how pacing pulses are output in response to sensed events and expiration of time intervals. The controller causes the pacing pulses to be output in response to lapsed time intervals and sensed electrical activity (i.e., intrinsic heart beats) in accordance with a programmed mode. Most pacemakers are programmed to operate in an inhibited demand mode (a.k.a., synchronous mode), where a pacing pulse is delivered to a heart chamber during a cardiac cycle only when no intrinsic beat by the chamber is detected. An escape interval is defined for each paced chamber, which is the minimum time interval in which a beat must be detected before a pace will be delivered. The ventricular escape interval thus defines the minimum rate at which the pacemaker will allow the heart to beat, sometimes referred to as the lower rate limit.

The pacemaker has an atrial sensing/pacing channel comprising ring electrode 33a, tip electrode 33b, sense amplifier 31, pulse generator 32, and an atrial channel interface 30 which communicates bidirectionally with a port of microprocessor 10. The device also has two ventricular sensing/pacing channels that similarly include ring electrodes 43a and 53a, tip electrodes 43b and 53b, sense amplifiers 41 and 51, pulse generators 42 and 52, and ventricular channel interfaces 40 and 50. For each channel, the electrodes are connected to the pacemaker by a lead and used for both sensing and pacing. A MOS switching network 70 controlled by the microprocessor is used to switch the electrodes from the input of a sense amplifier to the output of a pulse generator. The pacemaker also has an evoked response sensing channel that comprises an evoked response channel interface 20 and a sense amplifier 21 that has its differential inputs connected to a unipolar electrode 23 and to the device housing or can 60 through the switching network 70. As explained below, the evoked response sensing channel may be used to verify that a pacing pulse has achieved capture of the heart.

The channel interfaces include analog-to-digital converters for digitizing sensing signal inputs from the sensing amplifiers, registers that can be written to for adjusting the gain and threshold values of the sensing amplifiers, and, in the case of the ventricular and atrial channel interfaces, registers for controlling the output of pacing pulses and/or adjusting the pacing pulse energy by changing the pulse amplitude or pulse width. The microprocessor 10 controls the overall operation of the device in accordance with programmed instructions stored in memory. The sensing circuitry of the pacemaker generates atrial and ventricular sense signals when voltages sensed by the electrodes exceed a specified threshold. The controller then interprets sense signals from the sensing channels and controls the delivery of paces in accordance with a programmed pacing mode. The sense signals from any of the sensing channels of the pacemaker in FIG. 1 can be digitized and recorded by the controller to constitute an electrogram that can either be transmitted via the telemetry link 80 to the external programmer 300 or stored for later transmission.

b. Capture Verification and Capture Threshold Determination

A technique which can be used to determine if capture has been achieved during a given paced cardiac cycle is to look for an "evoked response" immediately following a pacing pulse. The evoked response is the wave of depolarization that results from the pacing pulse and evidences that the paced chamber has responded appropriately and contracted. By detecting an evoked atrial or ventricular depolarization that exceeds a specified value (i.e., corresponding to an evoked P-wave or evoked R-wave, respectively, on a surface electrocardiogram or their equivalents in an internal electrogram), one is able to detect whether the pacing pulse (A-pulse or V-pulse) was effective in capturing the heart, that is, causing a contraction in the respective heart chamber. An exemplary algorithm for determining the capture threshold (i.e., the minimum pacing pulse energy that results in capture) is as follows:

a) perform a capture verification test after delivery of a pacing pulse;
b) increase or decrease the pacing pulse energy by a specified amount if capture was absent or present, respectively, during the preceding capture verification test;
c) repeat the capture verification test with the increased or decreased pacing pulse energy;
d) determine the capture threshold as the pacing pulse energy before the decrease if the pacing pulse energy was decreased at step b and a loss of capture occurred during the repeated capture verification test, or repeating steps b through d otherwise.

The capture threshold determination procedure may be performed by adjusting the pacing pulse energy by changing the pulse width and/or the voltage amplitude. The value of the capture threshold determined in this manner varies with the individual patient, lead placement, and the type of leads employed. With modern leads, typical chronic capture threshold values for the voltage amplitude and pulse width of a minimum energy pacing pulse that achieves capture would be on the order of 1.0 volts and 0.5 milliseconds, respectively.

Capture verification and threshold determination can be performed in the clinical setting, with the clinician then adjusting pacing parameters so that the heart is reliably paced. It is desirable, however, for the pacemaker itself to be capable of verifying capture so that loss of capture can be detected when it occurs with pacing parameters then adjusted automatically, a function known as autocapture. (See, e.g., U.S. Pat. No. 6,169,921 issued to KenKnight, et. al., presently assigned to Cardiac Pacemakers, Inc. and hereby incorporated by reference.) An autocapture function provides the pacemaker with extended longevity, greater ease of use, and greater patient safety. The pacemaker controller may be programmed to perform capture verification tests on selected electrodes or pacing channels on a beat-to-beat basis, at periodic intervals, or in accordance with commands received via a telemetry link from an external programmer. If a loss of capture is detected, the controller can then perform a capture threshold determination and adjust the pacing pulse energy as appropriate. Loss of capture events may also be logged in the memory of the controller for later transmission to an external programmer.

An evoked response can be sensed with an sensing channel normally used for other purposes or a sensing channel dedicated to sensing evoked responses. In either case, the evoked response sensing channel is connected to a selected electrode of the pacemaker's sensing/pacing channels by means of a switching circuit. After switching the input of the evoked response sensing channel to the electrode that is to be tested to verify capture, a pacing pulse is output and an evoked response is either detected or not, signifying the presence or loss of capture, respectively. Although the same electrode can be used for pacing and evoked response detection during a capture verification test, the input of the evoked response sensing channel preferably is switched to an electrode of another sensing/pacing channel. The particular electrode used for evoked response detection can be selected in accordance with which electrode is placed in a location where an evoked response due to the pacing electrode can be most easily sensed.

In one method of capture verification, the evoked response is compared with a specified threshold value. The sense amplifier of the evoked response sensing channel is blanked during the capture verification test for a specified blanking period following a pacing pulse output by the tested sensing/pacing channel. The blanking period is followed by a capture detection window during which an evoked response may be sensed by the evoked response sensing channel. In an exemplary embodiment, the blanking period may be approximately 10 ms, and the width of the capture detection window may range from 50 to 350 ms. The amplitude of the evoked response signal during the capture detection window is then used to determine whether or not capture by the pacing pulse was achieved. Another way of performing a capture verification test involves recording an evoked response electrogram waveform during the pacing cycle and comparing the recorded waveform with a template waveform representing capture of the heart by a pacing pulse. The comparison between the template and evoked response waveforms may be done, for example, by time-domain cross-correlation. When performing capture verification in this fashion, it may be preferable to record the electrogram with a unipolar electrode that "sees" a larger volume of the myocardium as a wave of electrical activity spreads than a bipolar electrode. In the embodiment illustrated in FIG. 1, the atrial and ventricular sensing pacing channels utilize bipolar electrodes, and the dedicated evoked response sensing channel is provided with a unipolar electrode. Alternate embodiments may employ unipolar electrodes in the atrial and/or sensing/pacing channels, in which case unipolar sensing of an evoked response may be performed with those channels instead of a dedicated channel.

c. Pacing with Variable Safety Margin

In one of its aspects, the present invention involves optimizing the pacing pulse energy with a variable safety margin. It is known that the capture threshold for pacing pulses varies in accordance with the prior paced or intrinsic activity of the heart. In particular, capture by a pacing pulse is facilitated by prior pacing with capture as opposed to intrinsic activity. That is, the capture threshold at any point in time is greater if preceded by intrinsic beats than by paced beats. This phenomenon may be used to advantage by varying the pulse energy of pacing pulses (i.e., the pacing safety margin) in accordance with the pattern of prior intrinsic or paced beats.

Figure 2:
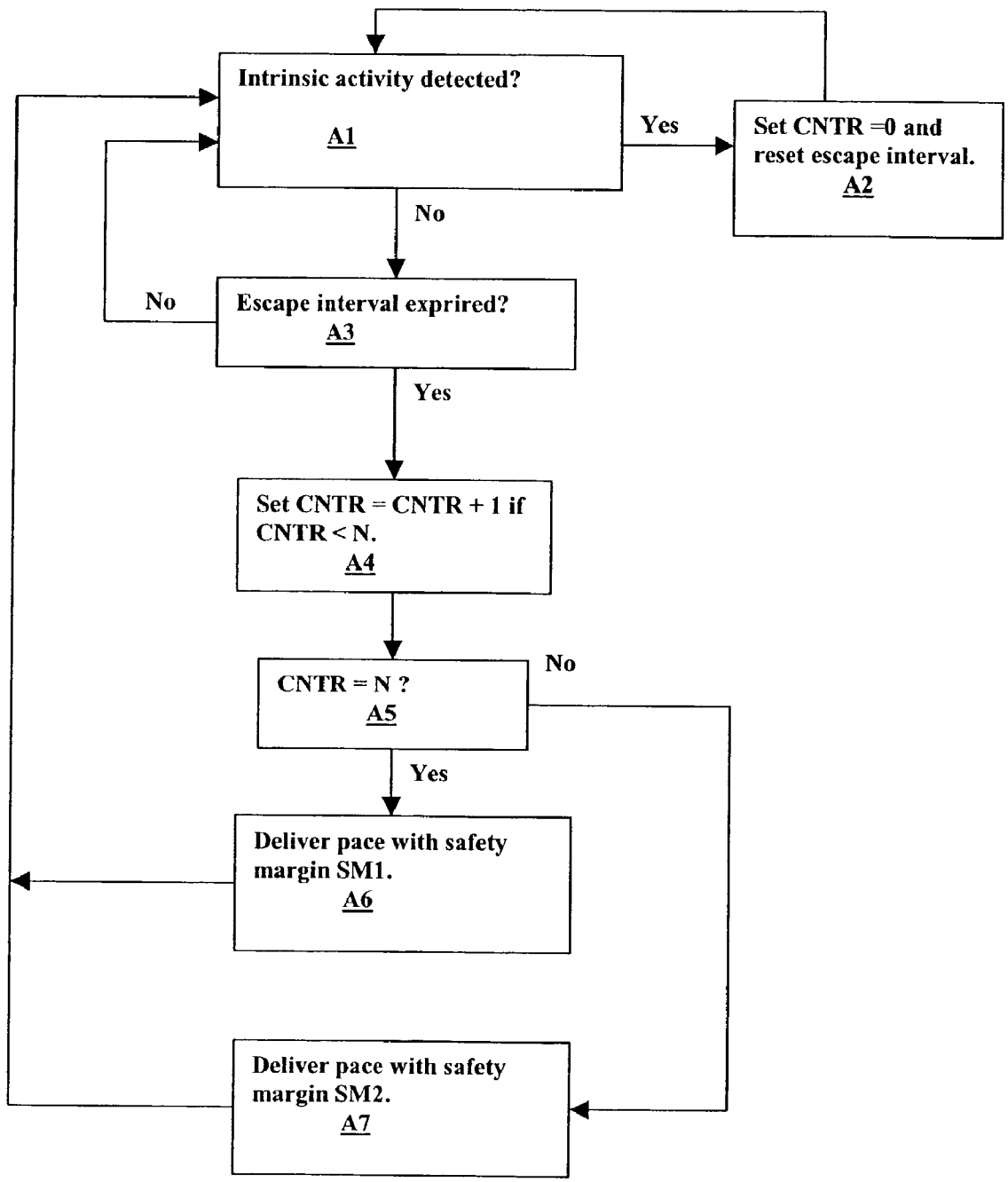
FIG. 2 is a flowchart of an exemplary implementation of a variable safety margin.

In an exemplary embodiment, two pacing safety margins, SM1 and SM2, are employed to deliver pacing pulses, where SM1 is less than SM2. Whenever a pace is first delivered after sensing intrinsic activity, the pace is delivered with a safety margin SM2. However, if pacing continues for a specified number N of paced beats, the safety margin is decreased to SM1. In an exemplary implementation, SM1 has a nominal value of 0.2 V, SM2 has a nominal value of 0.4 V, and N is equal to four. FIG. 2 shows a flowchart of this scheme in which a heart chamber is paced in an inhibited demand interval with a programmed escape interval. The paced heart chamber may be, for example, a ventricle, and the escape interval could be a ventricular escape interval or an atrio-ventricular interval in the case of atrial-tracking or AV sequential pacing. At step A1, intrinsic activity in the paced chamber is monitored. An escape interval timer runs until an intrinsic beat is detected, whereupon at step A2 the escape interval timer is reset. An integer variable CNTR is also cleared before returning to monitoring at step A1. If no intrinsic activity is detected, the escape interval timer is checked at step A3. The algorithm loops back to step A1 until the escape interval expires. Upon expiration of the escape interval, the variable CNTR is incremented at step A4 until it reaches the specified value N. The variable CNTR is then tested at step A5. If CNTR is equal to N, a pace is delivered at step A6 with safety margin SM1. If CNTR does not equal N, a pace is delivered at step A7 with safety margin SM2. The pacing pulse energy is thus decreased for those paces preceded by a specified number of consecutive paced beats.

In another aspect of the invention, the safety margins SM1 and SM2 are automatically adjusted in accordance with the results of capture verification tests performed during pacing, either on a beat-to-beat basis or periodically. SM1 is then increased if a pace delivered with safety margin SM1 fails to achieve capture, while SM2 is increased if a pace delivered with safety margin SM2 fails to achieve capture. The safety margins may be increased by fixed increments until a specified maximum value is reached. The device may be further programmed to decrease each safety margin gradually with each pace delivered with that safety margin until the pace fails to achieve capture.

Although the invention has been described in conjunction with the foregoing specific embodiment, many alternatives, variations, and modifications will be apparent to those of ordinary skill in the art. Such alternatives, variations, and modifications are intended to fall within the scope of the following appended claims.

What is claimed is:

1. A cardiac pacemaker, comprising:
   one or more sensing/pacing channels, each such channel comprising an electrode for disposing near a chamber of the head, a pulse generator for outputting pacing pulses, a sense amplifier for receiving voltage signals from the electrode, and a channel interface for adjusting the pacing pulse energy;
   a controller for controlling the operation of the pulse generators;
   circuitry for delivering one or more pacing pulses to a heart chamber during a cardiac cycle in accordance with an inhibited demand pacing mode; and,
   circuitry for delivering a pacing pulse to the heart chamber with a pulse energy selected to exceed a specified capture threshold value by a first safety margin SM1 if all of the preceding N cardiac cycles were paced cycles or by a second safety margin SM2 otherwise, where N is a specified integer.

2. The pacemaker of claim 1 wherein SM1 is less than SM2.

3. The pacemaker of claim 1 further comprising an evoked response sensing channel including an electrode and a sense amplifier for sensing an evoked response generated after a pacing pulse and further comprising circuitry for determining if a pacing pulse has achieved capture from the evoked response.

4. The pacemaker of claim 3 further comprising circuitry for determining if capture has been achieved by a pacing pulse by recording a test electrogram from the evoked response sensing channel and comparing the test electrogram with a template electrogram representing capture of the heart by at least one pacing pulse.

5. The pacemaker of claim 3 further comprising circuitry for determining if capture has been achieved by a pacing pulse by comparing the evoked response to a specified threshold value.

6. The pacemaker of claim 3 further comprising circuitry for determining if capture has been achieved by a pacing pulse during each cardiac cycle.

7. The pacemaker of claim 3 further comprising circuitry for increasing both safety margins SM1 and SM2 if capture was not achieved by a pacing pulse.

8. The pacemaker of claim 3 further comprising circuitry for increasing the safety margin SM1 if capture was not achieved by a pacing pulse delivered with the safety margin SM1.

9. The pacemaker of claim 3 further comprising circuitry for increasing the safety margin SM2 if capture was not achieved by a pacing pulse delivered with the safety margin SM2.

10. The pacemaker of claim 1 wherein the safety margins SMi and SM2 are initially specified with nominal values of 0.2 V and 0.4 V, respectively.

11. A method for operating a cardiac pacemaker, comprising:
    delivering one or more pacing pulses to a heart chamber during a cardiac cycle in accordance with an inhibited demand pacing mode; and,
    delivering a pacing pulse to the heart chamber with a pulse energy selected to exceed a specified capture threshold value by a first safety margin SM1 if all of the preceding N cardiac cycles were paced cycles or by a second safety margin SM2 otherwise, where N is a specified integer.

12. The method of claim 11 wherein SM1 is less than SM2.

13. The method of claim 11 further comprising sensing an evoked response generated after a pacing pulse and determining if a pacing pulse has achieved capture from the evoked response.

14. The method of claim 13 further comprising determining if capture has been achieved by a pacing pulse by recording a test electrogram from the evoked response sensing channel and comparing the test electrogram with a template electrogram representing capture of the heart by at least one pacing pulse.

15. The method of claim 13 further comprising determining if capture has been achieved by a pacing pulse by comparing the evoked response to a specified threshold value.

16. The method of claim 13 further comprising determining if capture has been achieved by a pacing pulse during each cardiac cycle.

17. The method of claim 13 further comprising increasing both safety margins SM1 and SM2 if capture was not achieved by a pacing pulse.

18. The method of claim 13 further comprising increasing the safety margin SM1 if capture was not achieved by a pacing pulse delivered with the safety margin SM1.

19. The method of claim 13 further comprising increasing the safety margin SM2 if capture was not achieved by a pacing pulse delivered with the safety margin SM2.

20. The method of claim 11 wherein the safety margins SM1 and SM2 are initially specified with nominal values of 0.2 V and 0.4 V, respectively.

* * * * *

UNITED STATES PATENT AND TRADEMARK OFFICE
CERTIFICATE OF CORRECTION

PATENT NO. : 7,158,831 B2 Page 1 of 1
APPLICATION NO. : 10/243622
DATED : January 2, 2007
INVENTOR(S) : Zhu It is certified that error appears in the above-identified patent and that said Letters Patent is hereby corrected as shown below:

In column 6, line 39, in Claim 1, delete "head" and insert -- heart --, therefor.

In column 6, line 54, in Claim 2, delete "SMI" and insert -- SM1 --, therefor.

In column 7, line 20, in Claim 10, delete "SMi" and insert -- SM1 --, therefor.

Signed and Sealed this

Fifteenth Day of May, 2007

JON W. DUDAS
*Director of the United States Patent and Trademark Office*